United States Patent [19]

Higdon

[11] Patent Number: 5,601,785

[45] Date of Patent: Feb. 11, 1997

[54] CONNECTOR FOR DETACHABLE COLUMN CARTRIDGE FOR GAS CHROMATOGRAPH

[75] Inventor: William R. Higdon, Pleasanton, Calif.

[73] Assignee: Microsensor Technology, Inc., Fremont, Calif.

[21] Appl. No.: 218,605

[22] Filed: Mar. 28, 1994

Related U.S. Application Data

[63] Continuation-in-part of Ser. No. 100,022, Jul. 30, 1993, Pat. No. 5,298,225, which is a continuation-in-part of Ser. No. 812,532, Dec. 23, 1991, Pat. No. 5,236,668.

[51] Int. Cl.$^6$ ...................................................... B01L 11/00
[52] U.S. Cl. .............................. 422/103; 422/70; 422/89; 73/23.42; 73/61.56; 96/106; 210/198.2; 285/177; 285/331; 285/382
[58] Field of Search ............................... 422/103, 89, 70; 73/23.42, 61.56; 96/106; 285/422, 423, 315, 331, 382, 182, 177, 915; 210/198.2

[56] References Cited

U.S. PATENT DOCUMENTS

| | | | |
|---|---|---|---|
| Re. 31,974 | 8/1985 | Brownlee . | |
| 2,718,485 | 9/1955 | Samuely | 154/126.5 |
| 2,992,457 | 7/1961 | Harrison | 18/59 |
| 3,213,596 | 10/1965 | Gill . | |
| 3,878,099 | 4/1975 | Ogle . | |
| 3,880,452 | 4/1975 | Fields | 285/177 |
| 3,996,017 | 12/1976 | Kaiser . | |
| 4,013,310 | 3/1977 | Dye | 285/177 |
| 4,083,702 | 4/1978 | Hartigan et al. . | |
| 4,116,836 | 9/1978 | DeAngelis . | |
| 4,173,363 | 11/1979 | Stearns | 285/177 |

(List continued on next page.)

FOREIGN PATENT DOCUMENTS

| | | | |
|---|---|---|---|
| 0087598 | 9/1983 | European Pat. Off. . | |
| 2207741 | 6/1974 | France | B01D 15/08 |
| 2256363 | 7/1975 | France . | |
| 2317654 | 2/1977 | France | G01N 31/08 |
| 2611908 | 9/1988 | France | G01N 30/02 |
| 3519725 | 12/1986 | Germany . | |
| 4114914 | 11/1992 | Germany . | |
| 4114914A1 | 11/1992 | Germany . | |
| 62-87857 | 4/1987 | Japan . | |
| 5-271626 | 10/1993 | Japan . | |
| 678055A5 | 7/1991 | Switzerland . | |
| WO89/07759 | 8/1989 | WIPO . | |
| WO90/06507 | 6/1990 | WIPO | G01N 30/60 |
| WO92/04958 | 4/1992 | WIPO . | |
| WO93/13415 | 7/1993 | WIPO . | |

OTHER PUBLICATIONS

Rondeau, M., "Revolutionary Process Called Swaging is Making its Mark", 2 pages.

Product literature entitled "Valdor Swage'n Crimp Connectors", 3 pages.

A. Spark, entitled "A Simple, Universal Joining System for Glass to Silica Capillary Tubing", Journal of High Resolution Chromatography & Chromatography Communications, pp. 481–482, 1986.

E. R. Rohwer et al., entitled "Simple Press–Fit Connectors for Flexible Fused Silica Tubing in Gas–Liquid Chromatography", Journal of High Resolution Chromatography & Chromatorgraphy Communications, pp. 295–297, 1986.

*Primary Examiner*—Jill Warden
*Assistant Examiner*—Jan M. Ludlow
*Attorney, Agent, or Firm*—Skjerven, Morrill, MacPherson, Franklin & Friel; David E. Steuber

[57] ABSTRACT

A detachable column cartridge for a gas chromatograph is disclosed. The cartridge column contains analytical and reference columns, a heater and a thermocouple, and connects via detachable connectors to a base unit containing an injector, a detector and other components normally found in gas chromatographs. The cartridge arrangement permits a substitute column to be connected to the base unit easily, in the field, when different gases are to be separated and analyzed. Also included are specific connectors for detachably connecting the columns with capillary tubes in the base unit of the gas chromatograph.

15 Claims, 9 Drawing Sheets

U.S. PATENT DOCUMENTS

| | | |
|---|---|---|
| 4,283,280 | 8/1981 | Brownlee . |
| 4,289,620 | 9/1981 | Hara . |
| 4,451,365 | 5/1984 | Sättler et al. . |
| 4,454,749 | 6/1984 | Guillemin et al. . |
| 4,478,715 | 10/1984 | Goodnight, Jr. . |
| 4,565,632 | 1/1986 | Hatch et al. . |
| 4,655,917 | 4/1987 | Shackelford et al. . |
| 4,669,756 | 6/1987 | Cassaday et al. . |
| 4,696,499 | 9/1987 | Butler .................. 285/234.4 |
| 4,758,340 | 7/1988 | Marchand et al. . |
| 4,776,618 | 10/1988 | Barree .................. 285/341 |
| 4,787,656 | 11/1988 | Ryder . |
| 4,968,421 | 11/1990 | Spacek et al. . |
| 4,969,938 | 11/1990 | America . |
| 5,105,652 | 4/1992 | Manfredi et al. . |
| 5,163,722 | 11/1992 | Worden .................. 285/375 |
| 5,234,235 | 8/1993 | Worden .................. 285/334.4 |
| 5,236,668 | 8/1993 | Higdon . |
| 5,288,113 | 2/1994 | Silvis et al. .................. 285/342 |
| 5,288,359 | 2/1994 | Stobble, IV et al. .................. 156/294 |
| 5,298,225 | 3/1994 | Higdon .................. 422/89 |

CONNECTOR FOR DETACHABLE COLUMN CARTRIDGE FOR GAS CHROMATOGRAPH

RELATED APPLICATIONS

This application is a continuation-in-part of application Ser. No. 08/100,022, filed Jul. 30, 1993, now U.S. Pat. No. 5,298,225, which is a continuation-in-part of application Ser. No. 07/812,532, filed Dec. 23, 1991, now U.S. Pat. No. 5,236,668.

FIELD OF THE INVENTION

This invention relates to gas chromatographs and in particular to miniature gas chromatographs having a capillary-type column and to connectors for such gas chromatographs.

BACKGROUND OF THE INVENTION

In recent years, semiconductor technology has created the possibility of a miniature gas chromatograph. Such a device is described in U.S. Pat. No. 4,474,889, issued to Terry et al., in which the channels for the carrier gas and sample gas are etched in a semiconductor wafer. The analytical column is external to these elements. U.S. Pat. No. 4,471,647, issued to Jerman et al., discloses a miniature gas chromatograph in which all of the channels, including the column, are etched on a semiconductor wafer.

Functionally, a gas chromatograph can be divided into elements which may be used repeatedly, for any tests, and elements which may need to be changed, depending on the gases to be detected. The former group includes the injector and detector and their associated valves and channels. On the other hand, the column may need to be changed in order to permit the gas chromatograph to analyze a different gas or group of gases.

The miniaturization of gas chromatographs has led to the use of miniaturized capillary columns having internal diameters generally in the range of 100–500 microns. Exchanging a column having these dimensions is no trivial task, and one that normally cannot be performed in the field. Frequently, the chromatograph must be returned to the manufacturer, who severs the connections to the analytical and reference lines at the injector and detector, replaces the column, and then reconnects the column to the injector and the detector. Aligning the tubes on either side of the connection is a delicate operation, and connectors containing ferrules are often used for this purpose. A mismatch or the introduction of a "dead volume" in the connector can create eddy currents and spatial voids which enhance Brownian diffusion, ultimately interfering with the accuracy of the analysis. This process can be time consuming and obviously requires the chromatograph to be removed from service. It also involves some expense and training.

SUMMARY OF THE INVENTION

A gas chromatograph in accordance with this invention includes two units: a base unit which contains injector and detector assemblies, manual controls and a visual display; and a column cartridge which contains capillary-type analytical and reference lines, a heater and a thermocouple. Connections between the column cartridge and the base unit are made with precisely machined connectors which are capable of providing a substantially perfect mating between the capillary tubes on either side of the connector, thereby providing a smooth flow of gases from the injector through the analytical and reference lines to the detector. An electrical connector provides connections for the heater and thermocouple. The cartridge is a completely self-contained unit which can simply be plugged into the base unit. The cartridges are interchangeable and can be replaced easily in the field, thereby eliminating the inconvenience and expense of returning the device to the manufacturer.

DESCRIPTION OF THE INVENTION

Figure 1:
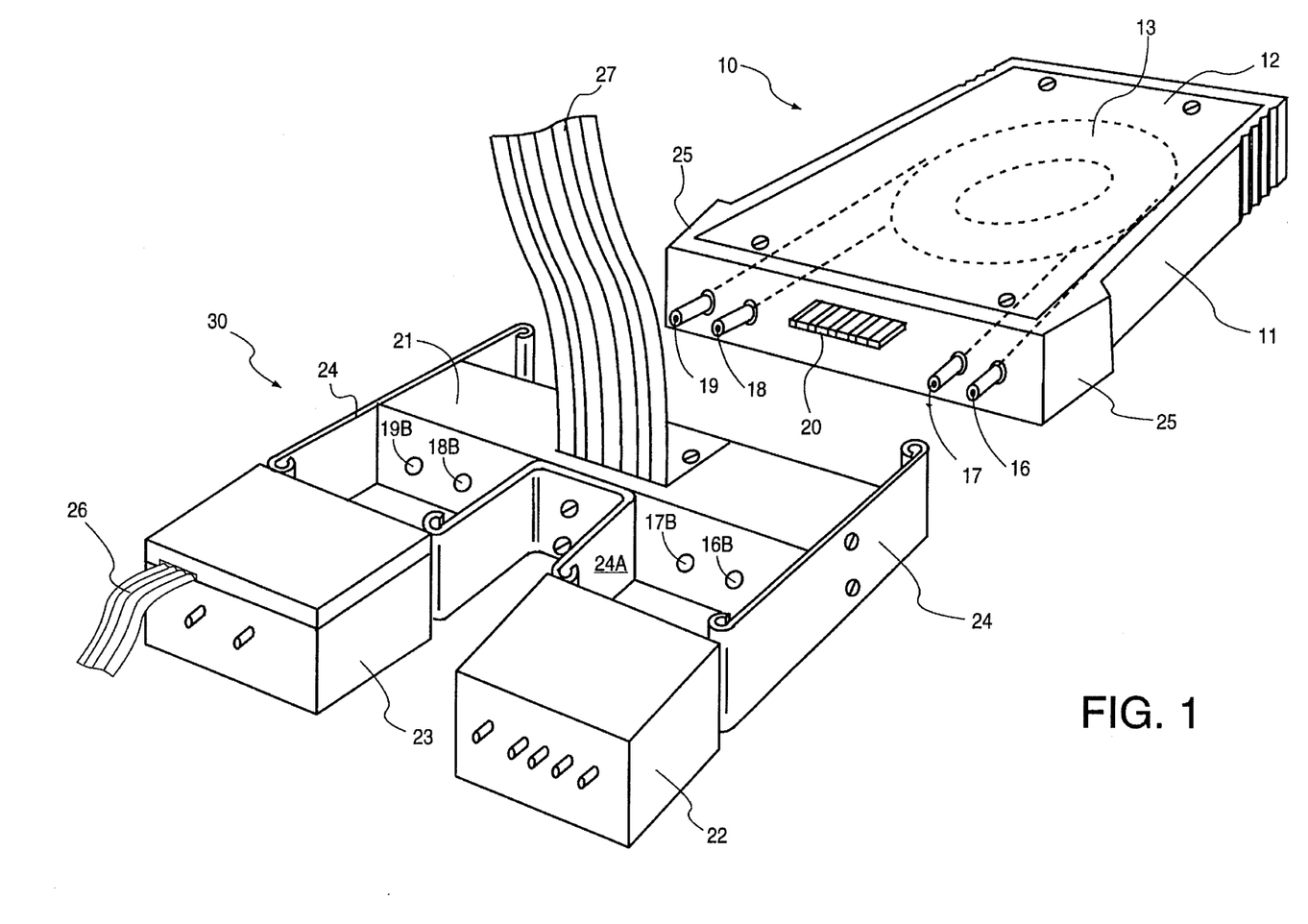
FIG. 1 is an isometric view of a column cartridge and a portion of a base unit in accordance with the invention.

FIG. 1 shows an isometric view of a column cartridge 10. The exterior of column cartridge 10 is formed by a housing 11 and a cover plate 12. A column 13 is placed inside housing 11 and positioned between insulation layers 14 (see FIG. 2B). Adjacent column 13 is a heater 15, which can more easily be viewed in FIG. 2A. The analytical and reference lines of column 13 terminate in male connectors 16 and 17, respectively, for connecting to an injector, and in male connectors 18 and 19, respectively, for connecting to a detector. A male connector 20 is provided for making the necessary electrical connections to heater 15 and a thermocouple (not shown), which is wound separately but adjacent to heater 15.

Also shown in FIG. 1 are a manifold block 21, a gas injector 22 and a solid state detector 23. Manifold block 21, injector 22 and detector 23 are components of a base unit 30 of a gas chromatograph, which contains manual controls, a visual display, and the other elements common to gas chromatographs (not shown). As indicated in FIG. 1, injector 22 and detector 23 are shown in an exploded view with respect to manifold block 21. In reality, injector 22 and detector 23 are connected with manifold block 21 in the manner described below.

Attached on either side of manifold block 21 are spring-loaded latch clips 24, the forward ends of which are formed so as to mate with detents 25 projecting from the sides of housing 11. Latch clips 24 are made of a spring metal so that cartridge 10 is securely fastened to base unit 30 when clips 24 are engaged with detents 25. The rear ends of latch clips 24 cooperate with a spring-loaded clip 24A to hold injector 22 and detector 23 against manifold block 21.

Figure 2A:
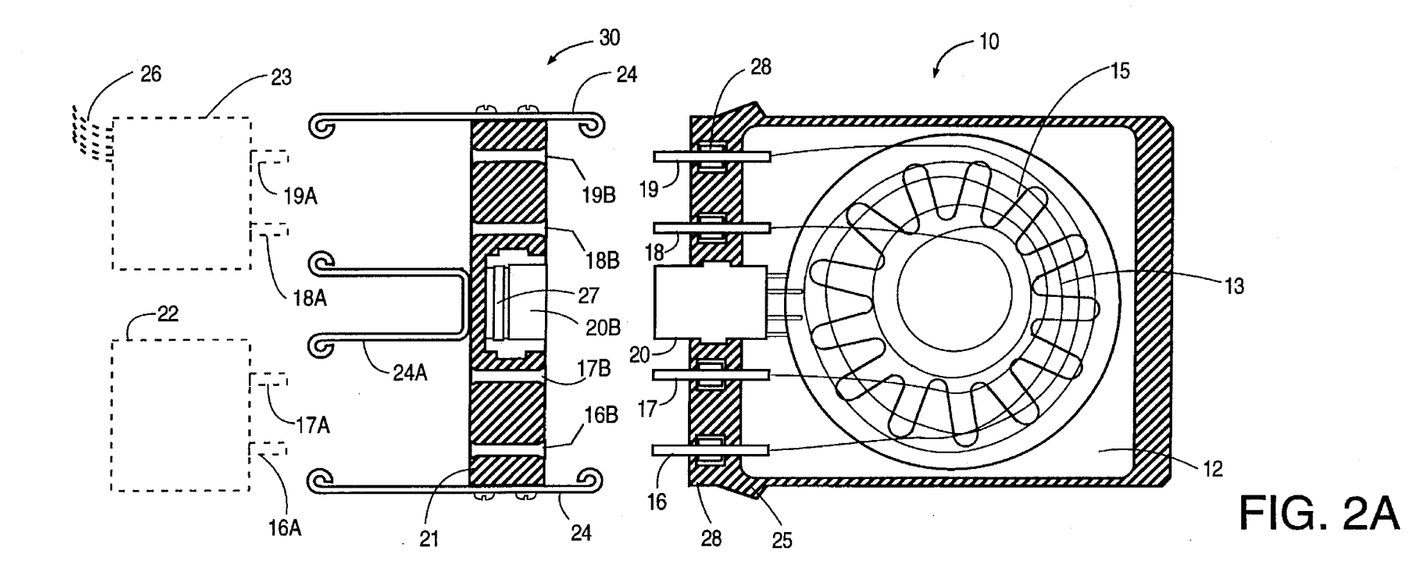
FIGS. 2A and 2B are top and side views, respectively of the column cartridge and base unit elements shown in FIG. 1.
Figure 2B:
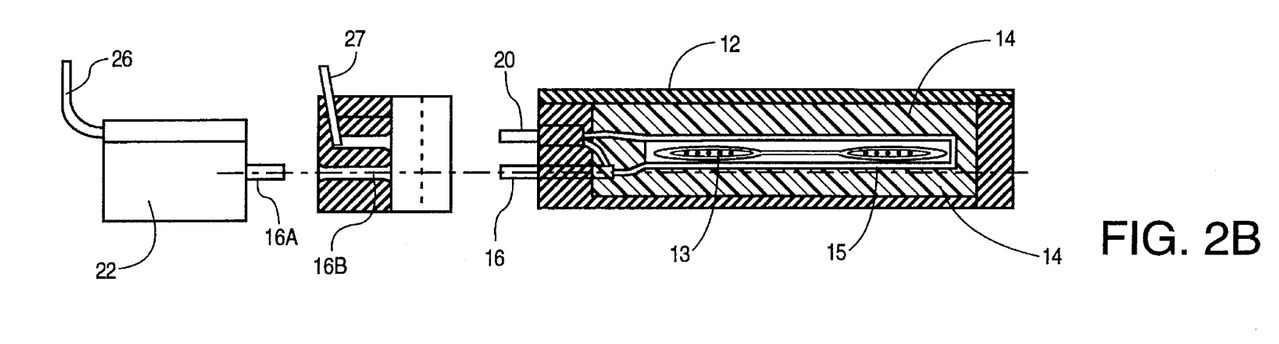

A ribbon-type electrical conductor 26 enters detector 23 from a printed circuit controller board (not shown). A second ribbon-type electrical connector 27 also extends from the printed circuit controller board and connects through manifold block 21 to connector 20. As shown in FIG. 2A, male connector 20 plugs into a female connector 20B in manifold block 21.

Manifold block 21 also contains holes 16B, 17B, 18B and 19B, which extend through the entire width of manifold block 21. Holes 16B–19B are spaced so as to coincide with connectors 16–19, and the diameter of holes 16B–19B is sized so as to allow a snug fit with connectors 16–19. Connectors 16A and 17A on injector 22 and connectors 18A and 19A on detector 23 are likewise spaced and sized so that they may be fitted into the opposite ends of holes 16B–19B.

Connectors 16–19 and 16A–19A are identical with each other. Connectors 16–19 are mounted in cavities 28 of housing 11, and connectors 16A–19A are mounted in similar cavities (not shown) in injector 22 and detector 23.

FIGS. 3 and 4A–4C show in detail how connectors 16–19 and 16A–19A are mounted, using connectors 16 and 16A as an illustration. As noted above, connector 16 is positioned in cavity 28 of housing 11. Similarly, connector 16A is positioned in a cavity 28A in a housing 22A of injector 22.

Figure 3:
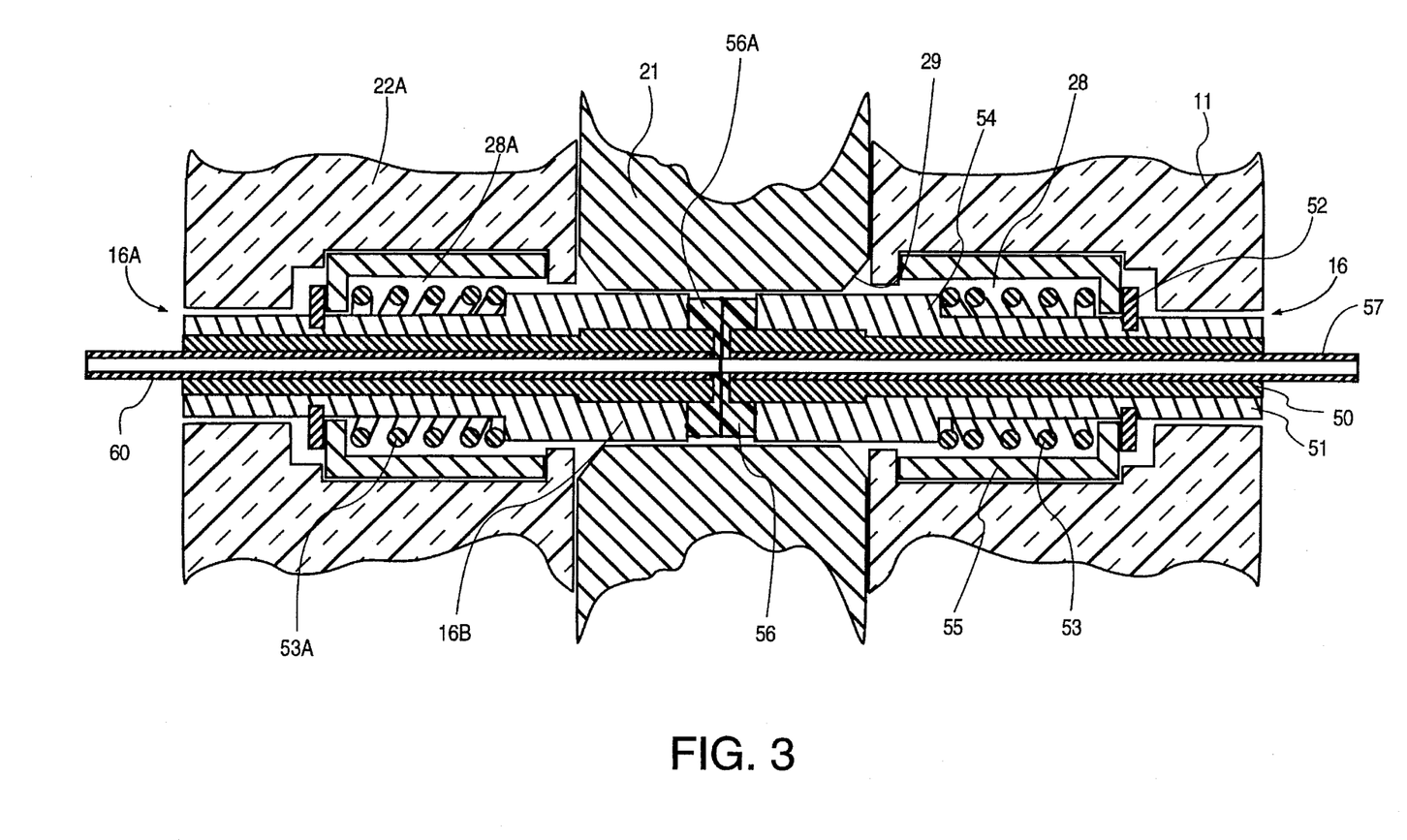
FIG. 3 is a detailed cross-sectional view of a column connector in accordance with the invention.

Since connectors 16 and 16A are identical, only connector 16 will be described in detail. The innermost part of connector 16 consists of a metal insert 50, which is surrounded by a polycarbonate sleeve 51. Sleeve 51 has a notch formed in its exterior circumference into which a C-ring clip 52 is snapped. A compression spring 53 surrounds sleeve 51 and engages a shoulder 54 of sleeve 51, forcing a spring housing 55 against C-ring clip 52. Cavity 28 is formed such that spring housing 55 is held firmly in place, while sleeve 51 and C-ring clip 52 are free to move a short distance to the right, as shown in FIG. 3.

One end of connector 16 projects from cartridge 10 (see FIG. 1) and is inserted into hole 16B in manifold block 21. A conical tapered surface 29 at the outside edge of hole 16B helps to guide connector 16 into hole 16B.

Figures 4A, 4B, 4C:
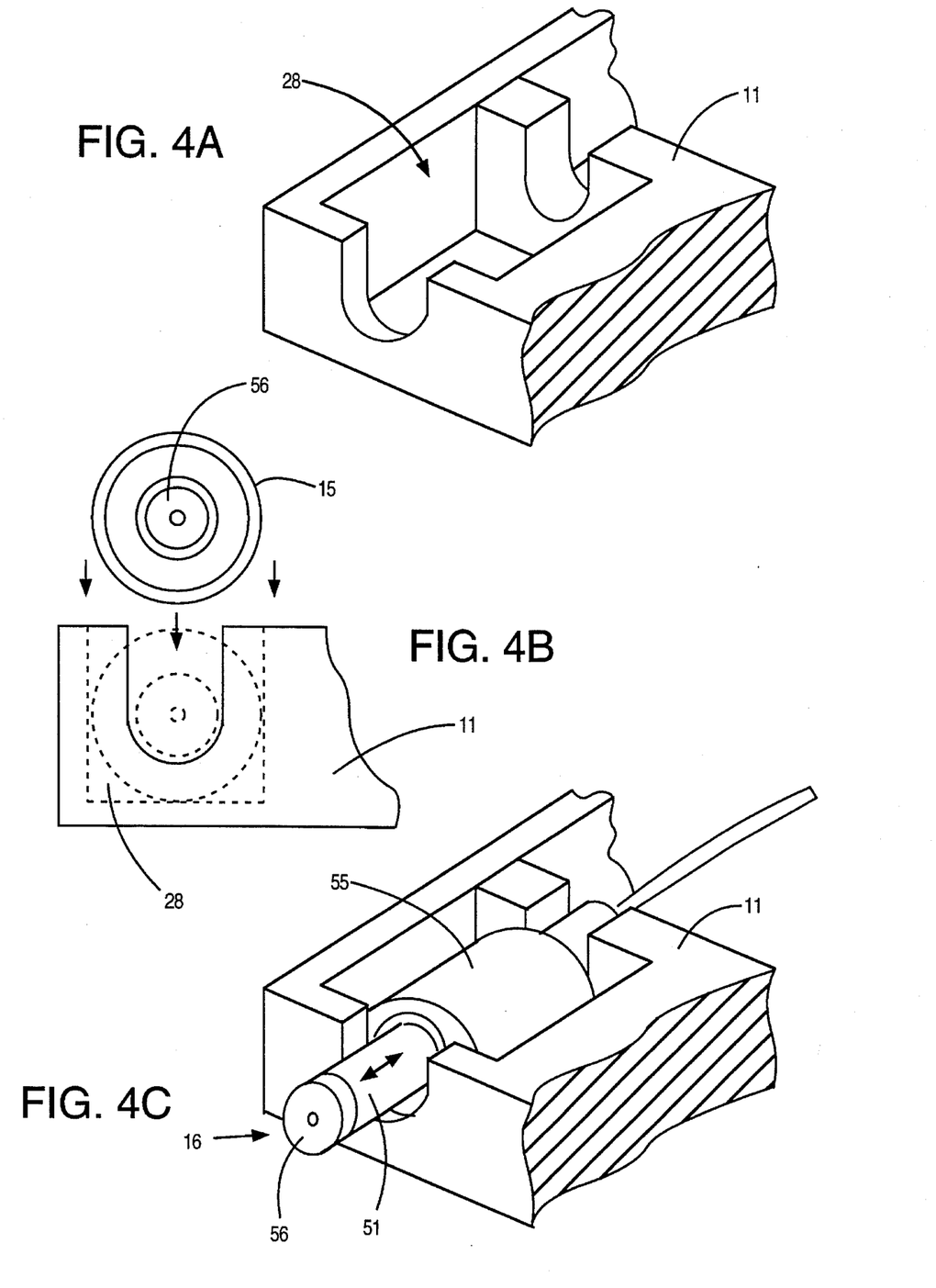
FIGS. 4A, 4B and 4C are additional views of the column connector and associated components shown in FIG. 3.

At the end of connector 16 which is inserted into hole 16B, metal insert 50 projects slightly beyond sleeve 51. An elastomeric gasket 56 is fitted over the projecting end of metal insert 50. (The structure of gasket 56 is shown in FIGS. 3 and 4C.) A hole is formed along the axis of metal insert 50, and this hole lines up perfectly with a hole formed in gasket 56 when gasket 56 is fitted over the end of metal insert 50. A polyimide-coated capillary column 57 is inserted into the hole in metal insert 50 until column 57 reaches the end of metal insert 50. Connector 16 is then heated to the melting point of the polyimide, causing the polyimide coating to bond column 57 to metal insert 50. A column 60 is similarly fitted into connector 16A.

As noted above, the structure of connector 16A is identical to that of connector 16. Because injector 22 is attached to manifold block 21, connector 16A is permanently fitted into hole 16B. Connectors 16 and 16A are positioned so that spring 53 and its counterpart spring 53A in connector 16A are compressed slightly when clips 24 engage detents 25, pressing housing 11 against manifold block 21. Accordingly, gasket 56 and its counterpart gasket 56A in connector 16A are compressed against each other forming a seal against the leakage of gas at the point where connectors 16 and 16A make contact.

In manufacturing this structure, it is very important that the axial holes in connectors 16 and 16A be machined accurately so that they are positioned at the axis of each connector. Similarly, the holes in gaskets 56 and 56A must be formed at the precise center of each gasket and must line up perfectly with the holes in connectors 16 and 16A. The holes in connectors 16 and 16A must allow a capillary column (such as column 57) to slide within them while firmly gripping the end of the column when it has been fully inserted. It has been found that this process is facilitated by tapering the holes slightly to a slightly smaller diameter at the end adjacent the elastomeric gasket. This ensures that the ends of columns 57 and 60 will be accurately aligned when cartridge 10 is attached to base unit 30.

Connectors suitable for use in this device are available from Valdor, Inc. of San Jose, Calif.

The structure of connectors 17–19 and 17A–19A is identical to that of connectors 16 and 16A. In a similar manner, they are fitted into holes 17B–19B in such a way that columns inserted into connectors 17–19 are lined up accurately with columns inserted into connectors 17A–19A.

Figure 5:
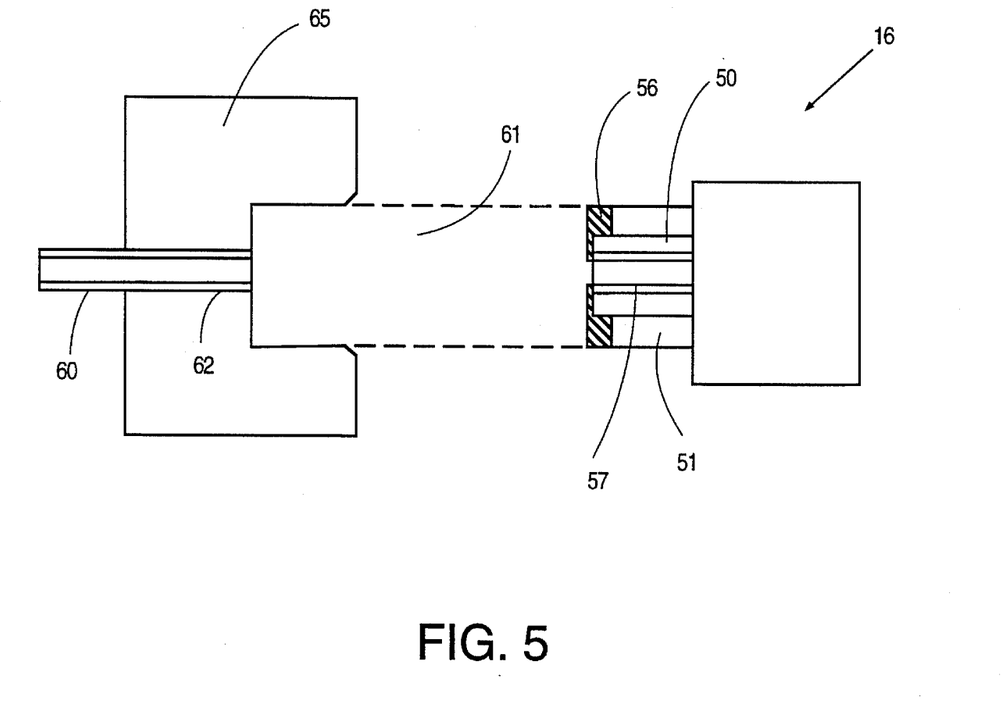
FIG. 5 is an illustration of an alternative embodiment in accordance with the invention.

An alternative structure for the connectors is illustrated in FIG. 5. In this embodiment, connector 16A is omitted, and a cylindrical cavity 61 is formed in a manifold block 65. The outside diameter of sleeve 51 is just slightly smaller than the inside diameter of cavity 61. A hole 62 for connector 60 is bored in manifold block 65, so that the axis of hole 62 and cavity 61 line up perfectly. When connector 16 is inserted into cavity 61, columns 57 and 60 line up perfectly, and gasket 56 is compressed against the rear wall of cavity 61, thereby creating a tight seal.

Figure 6:
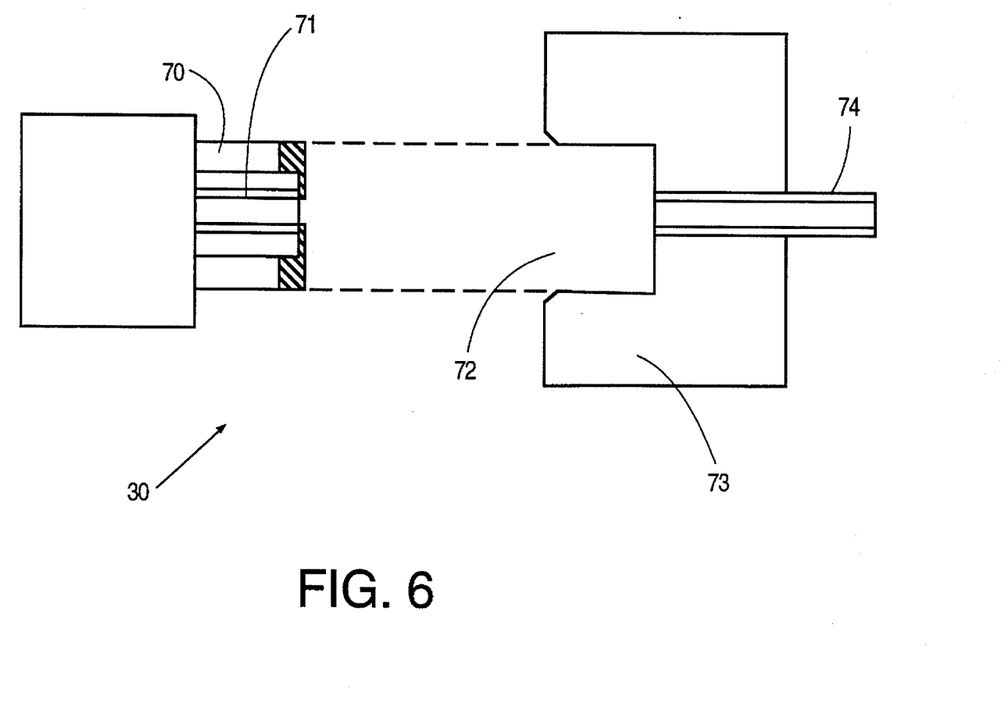
FIG. 6 is an illustration of another embodiment in accordance with the invention.

In another alternative structure the connector and cavity are essentially reversed, the connector being part of the base unit and the cavity being part of a detachable column cartridge. As shown in FIG. 6, a connector 70, which may be similar in every respect to connector 16, projects from base unit 30. A length of capillary tube 71 communicates with, for example, an injector and extends to the end of connector 70. A cavity 72 is formed in a cartridge housing 73, and one end of an analytical column 74 terminates at the rear wall of cavity 72. The other end of column 74 terminates at the rear wall of a similar cavity and forms a connection to a detector. Connector 70 may be spring-loaded in the same manner as connector 16, described above. Base unit 30 and cartridge housing 73 may be detachably connected with spring-loaded latch clips as shown in FIG. 2A.

Figure 7:
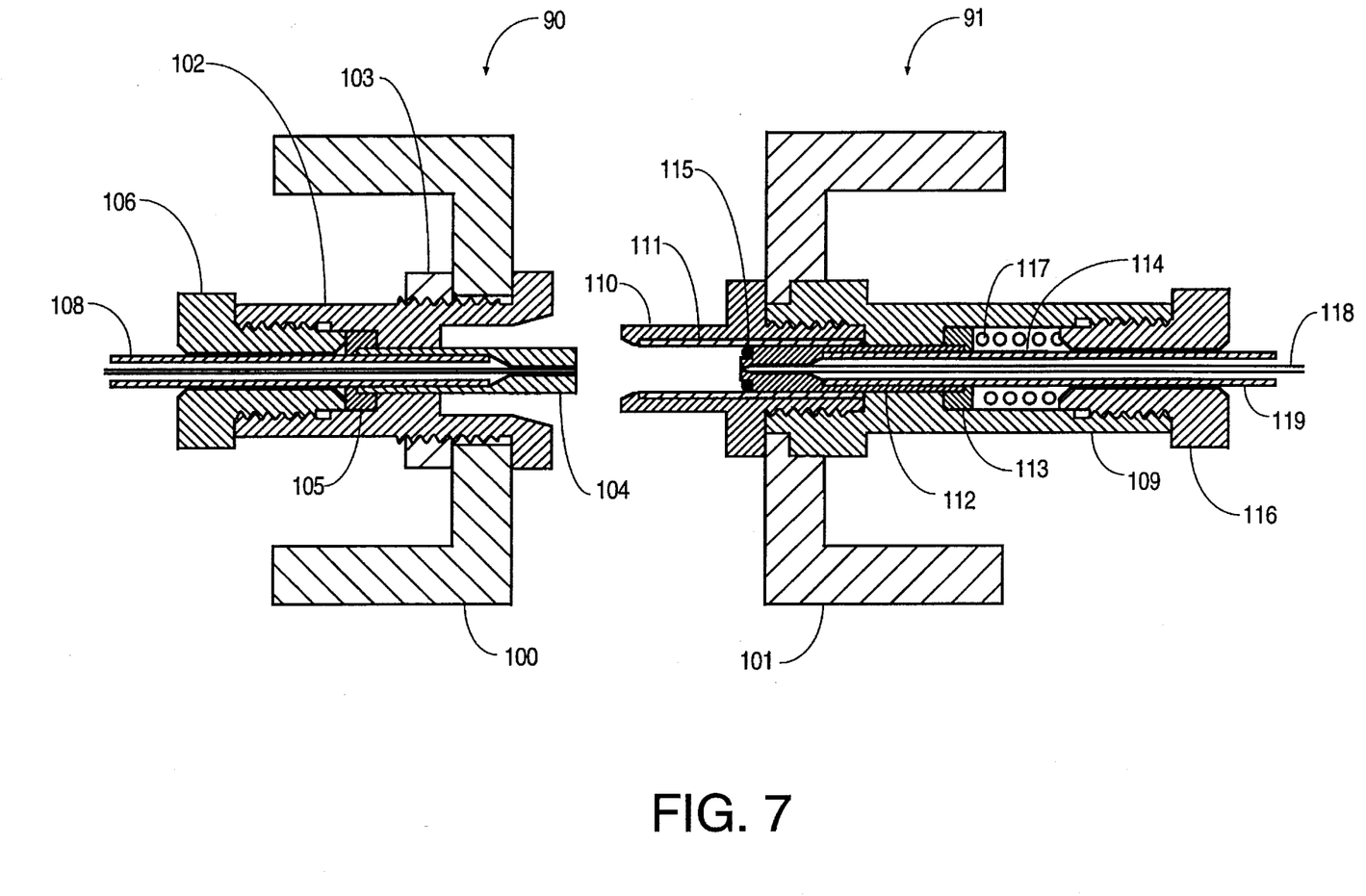
FIG. 7 is a cross-sectional view of yet another embodiment of a column connector in accordance with the invention, with the two sides of the connector separated.
Figure 8:
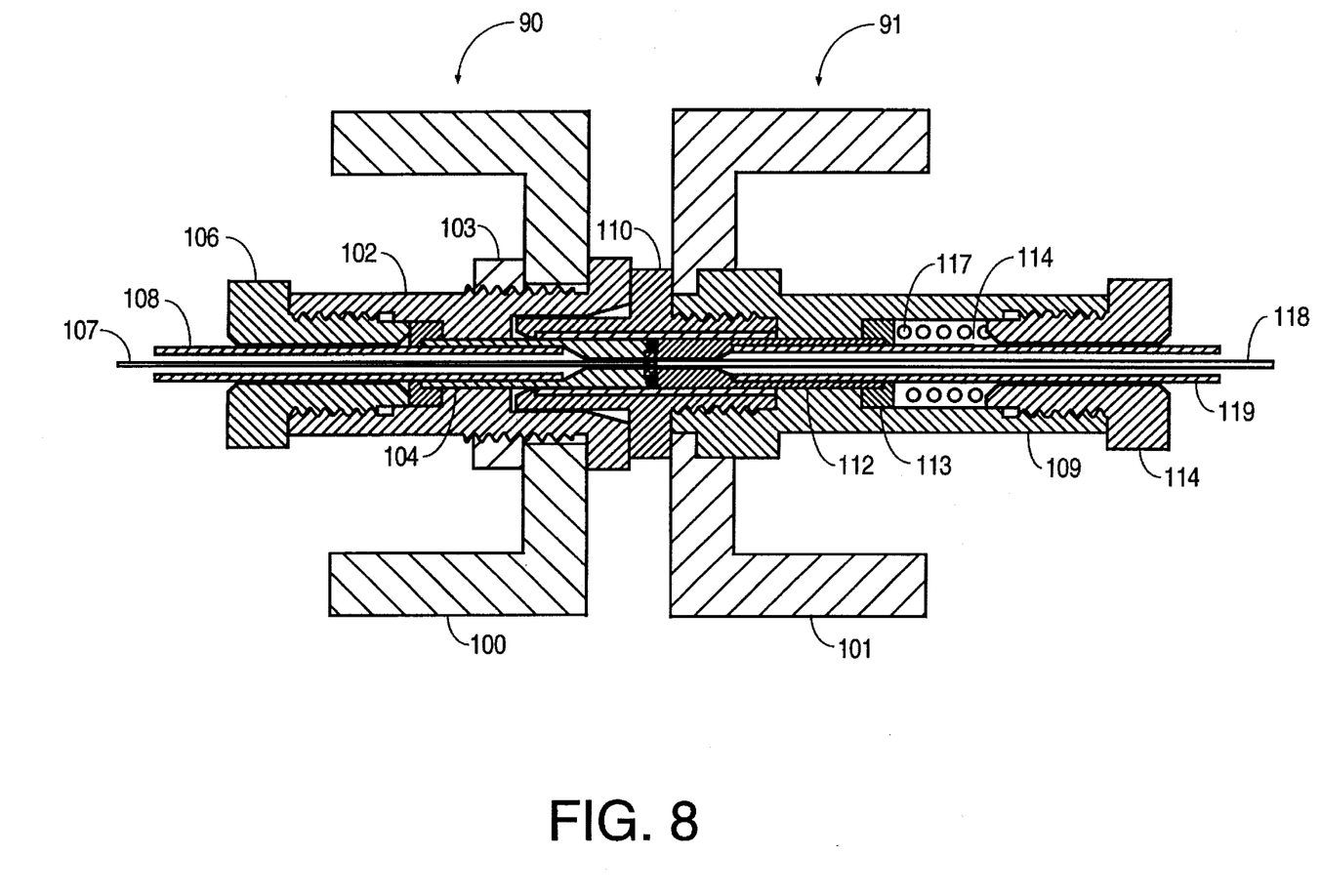
FIG. 8 is a cross-sectional view of the connector shown in FIG. 7 with the two sides of the connector joined.

FIGS. 7–11 illustrate yet another alternative column connector in accordance with the invention. FIGS. 7 and 8 show the overall structure of the column connector, with FIG. 7 showing the two sides 90 and 91 of the connector separated and FIG. 8 showing the two sides 90 and 91 of the connector joined. Referring to FIG. 7, reference numeral 100 refers to a male side bracket and reference numeral 101 refers to a female side bracket. It will be understood that brackets 100 and 101 could be attached to either a base unit or a column cartridge. In other words, the connector can be oriented with its male side connected to the base unit and its female side connected to the column cartridge, or vice versa.

Referring first to the male side 90 of the connector, bracket 100, which may be formed from an extruded aluminum channel, has a threaded bore into which is screwed an instrument guide 102. An instrument guide nut 103 is screwed onto instrument guide 102 to hold it in place within instrument bracket 100.

A cylindrical instrument fitting 104 has an end cap 105 attached to an end thereof, and is fitted into a central bore of instrument guide 102. End cap 105 is bonded to instrument fitting 104 with a high temperature glue or a ceramic cement, or any other high temperature resistant bonding method such as brazing, and is held in place within instrument guide 102 by an end plug 106. End plug 106 is screwed into a threaded bore on an end of instrument guide 102.

Instrument guide 102, guide nut 103, end cap 105 and end plug 106 are preferably made of stainless steel. Instrument fitting 104 is preferably made of zirconia but it could also be made of PYREX glass, quartz, alumina or other ceramic materials. A non-corrosive metal, such as stainless steel, or a moldable plastic, such as PEEK (polyetherether Ketone), could also be used for instrument fitting 104. End cap 105 could also be made of a ceramic material.

Instrument fitting 104 contains a narrow tapered bore into which a capillary tube 107 is fitted in a manner described below. To protect capillary tube 107 against bending stresses, a flexible strain relief 108 is inserted into a wider bore within instrument guide 104. The outside diameter of strain relief 108 is made slightly larger than the inside diameter of the wider bore within instrument guide 104 so that a snug fit is achieved. Strain relief 108 is preferably made of polyimide or TEFLON polymer.

The female side 91 of the connector includes a column guide 109, which is fitted into a two-diameter hole bored in column bracket 101. Column guide 109 is held in place by a column guide retainer 110, which is screwed into a threaded hole within column guide 109. A flange on column guide retainer 110 abuts bracket 101 and holds bracket 101, column guide 109 and column guide retainer 110 together as a unit. Column guide retainer 110 has an internal bore into which is fitted a split aligning sleeve 111. The length of sleeve 111 approximates the length of the central bore of column guide retainer 110. A column fitting 112 is inserted slideably into sleeve 111 and a central bore of column guide 109. An end cap 113 fits over an end of column fitting 112 and is positioned within a cavity 114 in column guide 109. Column fitting 112 has an annular notch at one end which holds an O-ring 115.

An end plug 116 is screwed into a threaded bore at an end of column guide 109 and thereby retains a compression spring 117 within cavity 114. A chromatographic column 118 is fitted into a tapered bore in column fitting 112, and a flexible strain relief 119 is fitted within a larger bore in column fitting 112.

The split aligning sleeve 111 should be loose inside column guide retainer 110 to allow for expansion when instrument fitting 104 and column fitting 112 are inserted within sleeve 111. Since sleeve 111 is split, it may expand slightly to provide a tight fit with instrument fitting 104 and column fitting 112 and thereby provide an accurate alignment of the tapered bores of fittings 104 and 112.

Column fitting 112 is preferably formed of the same material as instrument fitting 104. Column guide 109, column guide retainer 110, and end plug 116 are preferably made of stainless steel. Strain relief 119 may be made of polyimide or TEFLON polymer. O-ring 115 may be made of Viton, Silicone or TEFLON polymer. O-ring 115 may also be made of a metal or a plastic, such as PEEK or Vespel.

FIG. 8 illustrates male side 90 and female side 91 joined together. As shown, an extension of column guide retainer 110 fits within a bore in instrument guide 102. Column fitting 112 and end cap 113 slide a small distance to the right within sleeve 111 and column guide 109, compressing spring 117. The faces of instrument fitting 104 and column fitting 112 are pressed firmly together, creating a primary gas-tight seal surrounding the fluid flow path between capillary tube 107 and chromatographic column 118. O-ring 115 is also compressed, creating a secondary gas-tight seal. Male side 90 and female side 91 may be held together in a wide variety of ways including, for example, the latch clips 24 and detents 25 shown in FIG. 1.

Figure 9:
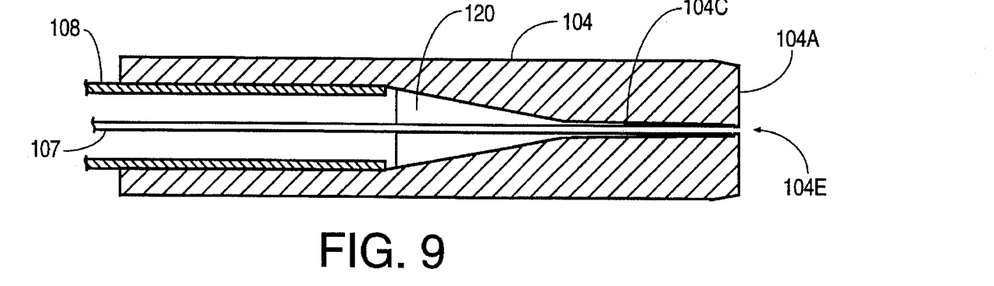
FIG. 9 is a cross-sectional view of the instrument fitting for the male side of the connector.
Figure 10:
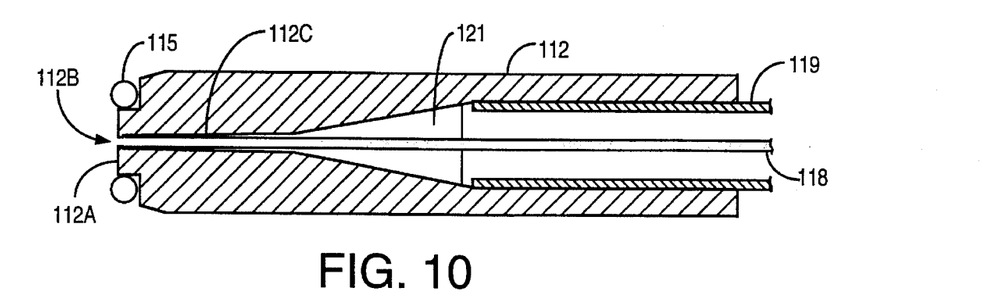
FIG. 10 is a cross-sectional view of the column fitting for the female side of the connector.
Figure 11:
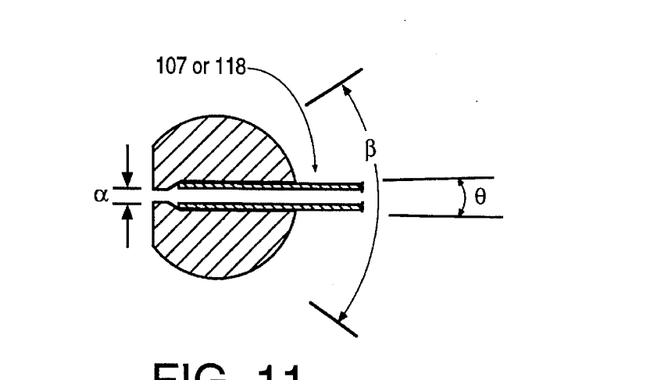
FIG. 11 is a detailed cross-sectional view of the mouth of the column and instrument fittings.

FIGS. 9–11 illustrate details of the structure of instrument fitting 104 and column fitting 112 and the manner in which capillary tube 107 and chromatographic column 118 are inserted into instrument fitting 104 and column fitting 112, respectively. Instrument fitting 104 and column fitting 112 have narrow tapered bore sections designated 104C and 112C, respectively, in FIGS. 9 and 10. Tapered bore section 104C ends in a orifice 104B at a face 104A of column fitting 104. Similarly, tapered bore section 112C terminates in an orifice 112B at a face 112A of column fitting 112. Instrument fitting 104 and column fitting 112 are preferably fabricated by injection molding and then machined to extremely accurate tolerances such that orifices 104B and 112B are on the central axes of instrument fitting 104 and column fitting 112, respectively. This is necessary to ensure that orifices 104B and 112B line up perfectly when male and female side of the connector are joined.

Capillary tube 107 has an external coating of polyimide. Tube 107 is inserted into the tapered section 104C until it approaches the orifice 104B, and an end of tube 107 abuts the walls of the tapered section 104C. Instrument fitting 104 is then heated to 200°–300° C. This fuses the coating of capillary column 107 to instrument fitting 104. Next, an adhesive, designated by the reference numeral 120, is introduced through the open end of instrument fitting 104 and is allowed to harden, firmly anchoring tube 107 to instrument fitting 104. The adhesive may be a high-temperature UV adhesive or it may be dissolved polyimide. Adhesive 120 may be extended to assist in holding strain relief 108 in place. Similarly, column 118 is forced into the tapered bore section 112C of column fitting 112 and an adhesive 121 is introduced.

FIG. 11 is a detailed view of the positioning of the capillary tube 107 and column 118 near orifices 104B and 112B. As shown, the tapered section is tapered at an angle $\theta$ which is preferably about 2½ degrees. The orifice is preferably constricted to a diameter d, which is equal to the inside diameter of the tube or column, and in any event should be no greater than the outside diameter of the tube or column. This minimizes any turbulence that is created as the gas flows between instrument fitting 104 and column fitting 112. The bore tapers to the constricted area at an angle $\beta$, which may be approximately 60 degrees.

The column or capillary tube is inserted until its end abuts the interior surface of the tapered bore. The dimensions of the tapered bore section should be keyed to the outside diameter of the particular column or capillary tube. Because of variations in the outer diameter of the tube, the end of the tube may reach refusal at various points within the tapered bore. However, for ruggedness and to minimize the chances of contaminating the fluid flow, the end of the column or capillary tube should be positioned as close as possible to the constricted end of the tapered bore.

Figure 12:
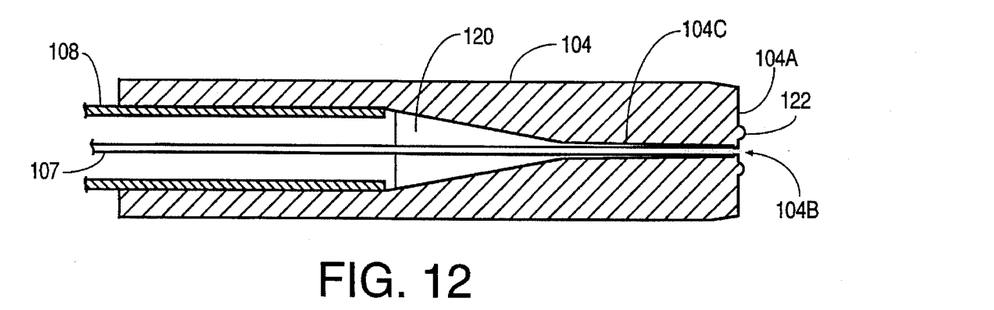
FIG. 12 is a cross-sectional view similar to FIG. 9 showing an embodiment with a raised ring on the face of the fitting.

Faces 104A and 112A should be perpendicular to the respective axes of instrument fitting 104 and column fitting 112, and should be polished to a 1 μm (or less) finish to achieve a gas tight seal. To improve the seal, it may be desirable to sputter or vacuum deposit a thin metal film on either or both of faces 104A and 112A. A film of gold, aluminum or nickel could be used for this purpose. Alternatively, a layer of TEFLON polymer or sealing materials commonly used in gas chromatography such as INCONEL, MONEL or HASTELOY alloys or polyimide could be applied to faces 104A and 112A. In some situations, it may be possible to omit O-ring 115, and rely solely on the contact of faces 104A and 112A to achieve a gas tight seal. Alternatively, as shown in FIG. 12, a raised ring 122 may be formed in one of faces 104A and 112A to concentrate the sealing force within a smaller area; or at least one of faces 104A and 112A may be formed with a slight curvature (arc) that becomes substantially flat when pressed against the opposing flat surface.

The foregoing embodiments are intended to be illustrative and not limiting. Numerous other embodiments will be apparent to those skilled in the art. For example, the principles of the invention are applicable to gas chromatographs which do not contain a Wheatstone Bridge type detector and therefore have no need for a reference column. All such alternative embodiments are included within the broad principles of the invention, as defined in the following claims.

I claim:

1. A connector joining two capillary tubes, said connector comprising:

first and second fittings, each of said first and second fittings having a tapered bore and an orifice at an end of said bore, said orifice being positioned on an axis of said fitting and on a surface of said fitting;

a first capillary tube inserted into said tapered bore of said first fitting;

a second capillary tube inserted into said tapered bore of said second fitting;

an end of said first capillary tube being spaced apart from said orifice of said first fitting and an end of said second capillary tube being spaced apart from said orifice of said second fitting, said orifice of said first fitting having a diameter no greater than an outside diameter of said first capillary tube and said orifice of said second fitting having a diameter no greater than an outside diameter of said second capillary tube;

a sleeve positioned so as to guide the surface of said first fitting into contact with the surface of the second fitting such that the orifice of the first fitting is aligned with the orifice of the second fitting, the contact between the surfaces of the first and second fittings creating a gas tight seal around said orifices.

2. The connector of claim 1 wherein a sealing layer is deposited on at least one of said surfaces, said layer comprising a material selected from the group consisting of gold, aluminum, nickel, tetrafluoroethylene polymer, polyetherether ketone, and polyimide.

3. The connector of claim 1 wherein a raised ring surrounding said orifice is formed in one of said flat surfaces.

4. The connector of claim 1 wherein said tapered bore is tapered at an angle of approximately 2½ degrees.

5. The connector of claim 1 wherein at least one of said capillary tubes comprises a chromatographic column.

6. The connector of claim 1 wherein said fittings comprise a ceramic material.

7. The connector of claim 6 wherein said fittings comprise a material selected from the group consisting of zirconia and alumina.

8. The connector of claim 1 wherein at least one of said capillary tubes has an exterior surface coated with a material which forms a bond between said capillary tube and one of said fittings.

9. The connector of claim 8 wherein said material comprises polyimide.

10. The connector of claim 1 wherein said surface of at least one of said fittings is flat.

11. The connector of claim 10 wherein said flat surface is perpendicular to said axis of said fitting.

12. The connector of claim 1 wherein said first fitting is mounted within a male side housing and said second fitting is mounted within a female side housing, said female side housing further comprising said sleeve.

13. The connector of claim 12 wherein an O-ring is fitted into an annular notch adjacent one of said surfaces.

14. The connector of claim 12 further comprising a means for holding said male side housing and said female side housing in juxtaposition.

15. The connector of claim 14 further comprising a spring for maintaining a pressure between said surfaces, said pressure being sufficient to create said gas tight seal.

* * * * *